(12) United States Patent
Saint-Remy et al.

(10) Patent No.: US 6,602,509 B1
(45) Date of Patent: *Aug. 5, 2003

(54) COMPOUND AND METHOD FOR THE PREVENTION AND/OR THE TREATMENT OF ALLERGY

(75) Inventors: Jean-Marie Saint-Remy, Grez-Doiceau (BE); Marc Jacquemin, Sart-Bernard (BE)

(73) Assignee: Leuven Research & Development VZW, Leuven (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/362,731

(22) Filed: Jul. 29, 1999

(30) Foreign Application Priority Data

Jul. 30, 1998 (EP) .......................... 98870167.8

(51) Int. Cl.⁷ .......................... A61K 39/35; C07K 1/02; C07K 14/00; C07K 19/00
(52) U.S. Cl. .............................. 424/275.1; 424/285.1; 530/324; 530/350
(58) Field of Search .................. 424/285.1, 275.1; 530/324, 350

(56) References Cited

U.S. PATENT DOCUMENTS 5,785,973 A * 7/1998 Bixler et al.

FOREIGN PATENT DOCUMENTS

| WO | 93/08279 | 4/1993 |
| WO | 95/31480 | 11/1995 |

OTHER PUBLICATIONS

Joel W. Goodman, PhD, "Immunogens & Antigens In: Stites dp, Terr Al, Prslow TG", editors Basic & clinical immunology, Eighth ed. Stamford: Appleton & Lange, 1994, p. 53–55.

Geoffery A. Mueller, et al., "Tertiary Structure of the Major House Dust Mite Allergen Der p 2: Sequential and Structural Homologies", Biochemistry 37, pp. 12707–12714 (1998).

Paola Panina–Bordignon et al. "Universally immunogenic T cell eptiopes: promiscuous binding to human MHC class II and promiscuous recognition by T cells", Eur. J. Immunol. 19, pp. 2237–2242 (1989).

Bo Wu et al., "Major T cell epitope–containing peptides can elicit strong antibody responses", Eur. J. Immunol. 30, pp. 291–299 (2000).

J. Duchateau et al., "Anti–betalactoglobulin IgG antibodies bind to a specific profile of epitopes when patients are allergic to cow's milk proteins", Clinical and Experimental Allergy, vol. 28, pp. 824–833 (1998).

* cited by examiner

*Primary Examiner*—Christina Chan
*Assistant Examiner*—Phuong N. Huynh
(74) *Attorney, Agent, or Firm*—Wenderoth, Lind & Ponack, L.L.P.

(57) ABSTRACT

The present invention is related to a compound for the prevention and/or the treatment of allergy consisting of:
  at least one allergen antigenic determinant which is recognized by a B cell or an antibody secreted by a B cell of a non-atopic individual to said allergen, and
  at least one antigenic determinant of an antigen different from said allergen which triggers T cell activation.

7 Claims, 5 Drawing Sheets

Reactivity of DerpII peptides with human IgE

Reactivity of DerpII with IgG of non-atopic subjects

Reactivity of DerpII peptides with IgG of atopic patients

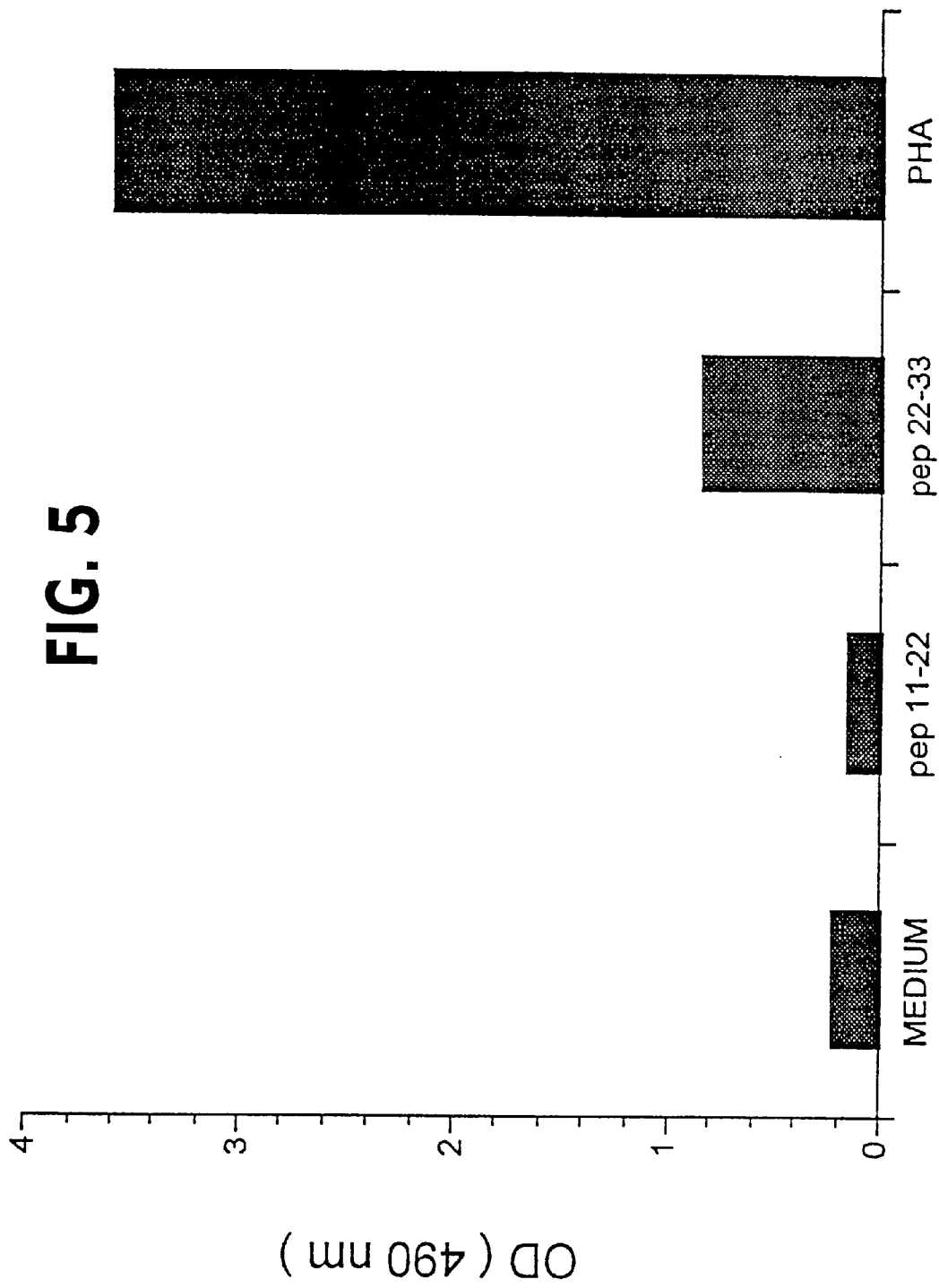

SEQUENCE LISTING

```
<160> NUMBER OF SEQ ID NOS: 18

<210> SEQ ID NO 1
<211> LENGTH: 31
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 1

Gln Tyr Ile Lys Ala Asn Ser Lys Phe Ile Gly Ile Thr Glu Leu Gly
 1               5                  10                  15

Gly His Glu Ile Lys Lys Val Leu Val Pro Gly Cys His Gly Ser
            20                  25                  30

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

His Glu Ile Lys Lys Val Leu Val Pro Gly Cys His Gly Ser
 1               5                  10
```

<210> SEQ ID NO 3
<211> LENGTH: 137
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Asp Gln Tyr Ile Lys Ala Asn Ser Lys Phe Ile Gly Ile Thr Glu Leu
 1               5                  10                  15

Gly Gly Gln Tyr Ile Lys Ala Asn Ser Lys Phe Ile Gly Ile Thr Glu
                20                  25                  30

Leu Ser Ser Cys His Gly Ser Glu Pro Cys Ile Ile His Arg Gly Lys
            35                  40                  45

Pro Phe Gly Gly Cys His Gly Ser Glu Pro Cys Ile Ile His Arg Gly
        50                  55                  60

Lys Pro Phe Ser Ser Cys His Gly Ser Glu Pro Cys Ile Ile His Arg
65                  70                  75                  80

Gly Lys Pro Phe Gly Gly Cys His Gly Ser Glu Pro Cys Ile Ile His
                85                  90                  95

Arg Gly Lys Pro Phe Ser Ser Cys His Gly Ser Glu Pro Cys Ile Ile
                100                 105                 110

His Arg Gly Lys Pro Phe Gly Gly Cys His Gly Ser Glu Pro Cys Ile
            115                 120                 125

Ile His Arg Gly Lys Pro Phe Ser Arg
        130                 135

<210> SEQ ID NO 4
<211> LENGTH: 40
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Pro Lys Tyr Val Lys Gln Asn Thr Leu Lys Leu Ala Thr Gly Lys Lys
 1               5                  10                  15

Gly Pro Lys Tyr Val Lys Gln Asn Thr Leu Lys Leu Ala Thr Gly Lys
                20                  25                  30

Lys Gly Val Ile Ile Gly Ile Lys
            35                  40

<210> SEQ ID NO 5
<211> LENGTH: 32
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5

Gln Tyr Ile Lys Ala Asn Ser Lys Phe Ile Gly Ile Thr Glu Leu Gly
 1               5                  10                  15

Gly Cys His Gly Ser Glu Pro Cys Asn Ile His Arg Gly Lys Pro Phe
                20                  25                  30

<210> SEQ ID NO 6
<211> LENGTH: 175

```
<212> TYPE: DNA
<213> ORGANISM: Artificial Sequence
<220> FEATURE:
<223> OTHER INFORMATION: Description of Artificial Sequence: synthetic
      nucleotidic sequence

<400> SEQUENCE: 6
gaattcccac catggatcag tatataaaag caaattctaa atttataggt ataactgaac      60
taggaggttg ccatggttca gaaccatgta tcattcatcg tggtaaacca ttcggcggtt    120
gtcacggaag tgagccttgc attatacaca gaggaaagcc gttctaagcg ccgc           175

<210> SEQ ID NO 7
<211> LENGTH: 53
<212> TYPE: DNA
<213> ORGANISM: Artificial Sequence
<220> FEATURE:
<223> OTHER INFORMATION: Description of Artificial Sequence: primer

<400> SEQUENCE: 7
gtatctctcg agaaaagaga tcaatacatt aaggctaaca gtaagttcat tgg             53

<210> SEQ ID NO 8
<211> LENGTH: 99
<212> TYPE: DNA
<213> ORGANISM: Artificial Sequence
<220> FEATURE:
<223> OTHER INFORMATION: Description of Artificial Sequence: primer

<400> SEQUENCE: 8
aaacagcctc tagagagttc ggtaatgccg ataaactttg aattggcttt gatgtactga     60
ccgccaagct ctgtgattcc aatgaactta ctgttagcc                             99

<210> SEQ ID NO 9
<211> LENGTH: 103
<212> TYPE: DNA
<213> ORGANISM: Artificial Sequence
<220> FEATURE:
<223> OTHER INFORMATION: Description of Artificial Sequence: primer

<400> SEQUENCE: 9
gtatctacta gttgccatgg ttcagaacca tgtatcattc atcgtggtaa accattcggc     60
ggttgtcacg gaagtgagcc ttgcattata cacagaggaa agc                       103

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 10
cgtatgtgtc gacccgctat ctagagaacg gctttcctct gtgtataatg c               51

<210> SEQ ID NO 11
<211> LENGTH: 103
<212> TYPE: DNA
<213> ORGANISM: Artificial Sequence
<220> FEATURE:
<223> OTHER INFORMATION: Description of Artificial Sequence: primer

<400> SEQUENCE: 11
ccggaattcc caccatggat cagtatataa agcaaattc taaatttata ggtataactg      60
aactaggagg ttgccatggt tcagaaccat gtatcattca tcg                       103
```

<210> SEQ ID NO 12
<211> LENGTH: 105
<212> TYPE: DNA
<213> ORGANISM: Artificial Sequence
<220> FEATURE:
<223> OTHER INFORMATION: Description of Artificial Sequence: primer

<400> SEQUENCE: 12
tcgagcggcc gcttagaacg gctttcctct gtgtataatg caaggctcac ttccgtgaca      60
accgccgaat ggtttaccac gatgaatgat acatggttct gaacc      105

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 13

Gln Tyr Ile Lys Ala Asn Ser Lys Phe Ile Gly Ile Thr Glu Leu
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Cys His Gly Ser Glu Pro Cys Asn Ile His Arg Gly Lys Pro Phe
 1               5                  10                  15

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 15

Thr Ala Gly Gly Cys Gly Gly Cys Cys Gly Cys
 1               5                  10

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: KOZAK
      sequence

<400> SEQUENCE: 16
gaattcccac catgg      15

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Sequence
      containing stop codon and Not1 restriction site

```
-continued

<400> SEQUENCE: 17
taggcggccg c                                                          11

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 18

Pro Lys Tyr Val Lys Gln Asn Thr Leu Lys Leu Ala Thr
  1               5                  10
```

COMPOUND AND METHOD FOR THE PREVENTION AND/OR THE TREATMENT OF ALLERGY

This application claims Foreign Priority under 35 USC §119 (a–d) of EPO Application No. 98870167.8 filed Jul. 30, 1998.

BACKGROUND OF THE INVENTION

1. Field of the Invention

The present invention is related to a new compound and a new method for the prevention and/or the treatment of allergy and/or diseases of allergic origin, particularly immediate hypersensitivity allergy.

2. Description of the Related Art

Immediate hypersensitivity is a form of allergic reaction which develops very quickly, namely within seconds or minutes of exposure of the patient to the causative allergen. This immediate reaction can be followed by a second reaction of delayed onset that can lead to inflammatory changes in the target organ and manifests itself by chronic symptoms such as asthma or atopic dermatitis.

Immediate hypersensitivity is mediated by antibodies belonging mainly, but not exclusively, to the IgE isotype. IgE antibodies bind to specific receptors on cells such as basophils, mastocytes or Langerhans' cells. Upon allergen exposure, surface-bound IgE transduce a signal into the cell, which is followed by cell activation, which in the case of basophils and mastocytes is accompanied by the release of preformed mediators such as histamine and enzymes, and the synthesis of metabolites of arachidonic acid. These mediators are responsible for the development of allergic signs and symptoms, such as bronchospasm, vasodilatation, hypersecretion of mucus and stimulation of sensory nerve ends resulting in pruritus.

IgE antibodies are produced by B lymphocytes that received appropriate activation signals. Full description of the mechanisms by which IgE antibodies are produced can be found in appropriate reviews (see for instance Vercelli D., *Allergy Proc.* 14, pp. 413–416 (1993)).

Current treatment of allergic symptoms include allergen avoidance, drug therapy and immunotherapy. Complete avoidance from allergen exposure is the most logical approach, but it remains very difficult, or impossible to achieve in a vast majority of cases. Drug therapy is useful, but alleviates the symptoms without influencing their causes. In addition, drug treatment is usually limited by undesirable side-effects.

Current approaches for immunotherapy are:

1) conventional hyposensitisation which is a treatment consisting in administering to the patient progressively increasing doses of the allergen(s) to which he has developed a sensitivity;
2) allergen alteration aiming at reducing recognition by specific antibodies, IgE in particular;
3) allergen-derived peptides used to interfere in the cognate interaction between specific B and T cells or containing an IgE-binding B cell epitope.

Such allergen-derived peptides containing one or a few T cell epitope(s) used in animal experiments and in human beings in an attempt to inhibit specific T cell activation and induce a state of T cell unresponsiveness, are described in the patent application WO93/08279.

One human application of this concept is the administration of a peptide derived from the sequence of T cell epitopes present on the Fel dI allergen, by subcutaneous injections in cat-sensitive individuals (Wallner B. P., Gefter M. L., *Allergy* 49, pp. 302–308 (1994)). An alternative, complementary approach of this concept has also been used in animal experiments. The peptides used are modified in such a manner as to keep the ability to bind to MHC-class II determinants on specific B cells, but which have lost their capacity to activate the corresponding T cells (O'Hehir R. E. et al., *International Immunology* 3, pp. 819–826 (1991)).

It is known that allergic reactions are generated by the liberation of mediators from target cells, such as basophils or mastocytes, having high-affinity surface receptors for IgE, which are occupied by IgE antibodies. The minimum requirement for mediator liberation to occur is that two IgE molecules recognising the same allergen are cross-linked, which in turn cross-link the receptor, resulting in the transduction of an activating signal within the cell. If only one IgE molecule is able to bind the allergen, no cell activation ensues, but the binding site of the IgE would be occupied, preventing cell activation upon exposure to native allergen. The use of a single IGE-binding epitope has therefore been claimed to be a suitable approach for the treatment of allergic diseases (Ball T. et al., J. Biol. Chem. 269, pp. 28323–28328 (1994), EP-A-0714662).

U.S. Pat. No. 4,946,945 describes a protein conjugate useful in immunotherapy, composed of a biological response modifier (BRM) and an allergen. Said conjugate could be combined with a pharmaceutically acceptable carrier. Cytokin, bacterial, fungal and viral immunopotentiators and thymus hormones are disclosed as suitable BRMs for use in said document.

The patent application WO95/31480 describes the preparation and the use of a synthetic compound made of two alpha-helices with specific arrangements of various amino acids. Said compound is used as a support for the binding of functional units, especially epitopes B and/or T.

It is meant by "atopy", a predisposition, partly of genetic origin, of an individual having an immune system producing an excess of antibodies belonging to the IgE isotype in response to exposure to allergens. Individuals presenting such characteristics are therefore called "atopics".

An "allergen" is defined as a substance, usually a macromolecule of proteic composition, which elicits the production of IgE antibodies in predisposed, preferably genetically disposed, individuals (atopics).

Similar definitions are presented in the following references: *Clin. Exp. Allergy*, No. 26, pp. 494–516 (1996); *Mol. Biol. of Allergy and Immunology*, ed. R. Bush, *Immunology and Allergy Clinics of North American Series* (August 1996).

These allergens are preferably the main allergens which are selected from the group consisting of:
food allergens present in peanuts, codfish, egg white, soybean, shrimp, milk and wheat,
house dust mites allergens obtained from Dermatophagoides spp. pteronyssinus, farinae and microceras, *Euroglyphus maynei* or Blomia,
allergens from insects present in cockroach or hymenoptera,
allergens from pollen, especially pollens of tree, grass and weed,
allergens present in animals, especially in cat, dog, horse and rodent,
allergens present in fungus, especially from Aspergillus, Alternaria or Cladosporium, and
occupational allergens present in such products as latex, amylase, etc.

Said allergens can also be main allergens present in moulds or various drugs such as hormones, antibiotics, enzymes, etc.

"Allergy" is the ensemble of signs and symptoms which are observed whenever an atopic individual encounters an allergen to which he has been sensitised, which may result in the development of various diseases and symptoms such as allergic rhinitis, bronchial asthma, atopic dermatitis, etc.

"Hypersensitivity" is an untoward reaction produced in a susceptible individual upon exposure to an antigen to which he has become sensitised; immediate hypersensitivity depends of the production of IgE antibodies and is therefore equal to allergy.

It is meant by the terms "epitope" or "antigenic determinant", one or several portions (which may define a conformational epitope) of an antigen (structure of a macromolecule, including an allergen, preferably made of proteic composition but also made of one or more hapten(s) or portion of a pharmaceutical active compound) which are specifically recognised and bound by an antibody or a receptor at the cell surface of a B or T lymphocyte.

SUMMARY OF THE INVENTION

The purpose of the present invention is to provide a vaccination strategy by which the antibody response made by atopic individuals against allergens is deviated from the allergen major determinants that are spontaneously recognised by atopic individuals, to determinants on the same molecule that are spontaneously recognised by antibodies of non-atopic individuals, or to determinants which are not spontaneously recognised by the majority of individuals, independently of their atopic status.

The present invention is related to a compound comprising either

- at least one allergen antigenic determinant which is recognised by a B cell or antibody secreted by a B cell of a non-atopic (to said allergen) individual (including cryptic determinant which is not recognised by atopics individuals, and minimally recognised by non-atopics individuals) and which is preferably not recognised by a T cell, and at least one antigenic determinant of an antigen different from said allergen, said antigenic determinant triggering T cell activation, or
- a nucleotide sequence encoding said both antigenic determinants, said sequence being possibly linked to one or more regulatory sequence(s) active into a patient's cell.

The specific allergen antigenic determinants present in known main allergens are easily identified by the person skilled in the art, who may select said epitopes or antigenic determinants of said allergen which are recognised by non-atopic individuals (non-atopic individuals to said allergen) and which may differ from the other epitopes for which atopic individuals produce antibodies as above-described. Similarly, the person skilled in the art may select the specific antigenic determinant of any antigen (different from said allergen) which is known to trigger T cell activation. Preferably, said antigen is not an allergen. A preferred selection of this epitope is described in the examples presented hereafter.

The compound according to the invention will produce in atopic patients a shift of the anti-allergen immune response towards epitopes or antigenic determinants that are not spontaneously or only minimally recognised by antibodies of atopic patients.

In the compound according to the invention, the allergen antigenic determinant and the antigenic determinant of the non-allergic antigen are preferably peptidic sequences chemically bound together (in a linear tandem form or branched form), preferably by a peptidic link, which is preferably made of at least two amino-acids. The compound according to the invention is in a linear or a cyclic form, with or without additional moieties used, for instance to block peptide—peptide interactions.

Advantageously, the allergen is selected from the group consisting of Der pI and Der pII of house dust mite *Dermatophagoides pteronyssinus*, the major antigen of *Aspergillus fumigatus*, the staphylococcal B enterotoxin (SEB) and the bovine β-lactoglobulin or the allergen described in the documents *Clin. Exp. Allergy*, No. 26, pp. 494–516 (1996); *Mol. Biol. of Allergy and Immunology*, ed. R. Bush, *Immunology and Allergy Clinics of North American Series* (August 1996).

Advantageously, in the compound according to the invention, the antigenic determinant of an antigen which triggers T cell activation is a T cell epitope (preferably a helper T cell epitope) of tetanus toxoid, diphtheria, mycobacterium, influenza or measles viruses antigens (other examples of said T cell epitopes are described in the table II of the document WO95/26365).

Preferably, the compound according to the invention is selected from the group consisting of the peptides having the following amino acid sequences:

SEQ ID NO. 1:
  QYIKANSKFIGITELGGHEIKKVLVPGCHGS

SEQ ID NO. 2:
  HEIKKVLVPGCHGS

SEQ ID NO. 3:
  D Q Y I K A N S K F I G I T E L G G Q Y I K A N-
  S K F I G I T E L S S C H G S E P C I I H R G K P F G-
  GCHGSEPC IIHRGKPFSSCHGSEPCIIHRGK-
  PFGGCHGSEPCIIHRGKPFSSCHGSEPCIIHRGKPF
  GGCHGSEPCIIHRGKPFSR

SEQ ID NO. 4:
  P K Y V K Q N T L K L A T G K K G P-
  KYVKQNTLKLATGKKGVIIGIK

SEQ ID NO. 5:
  QYIKANSKFIGITELGGCHGSEPCNIHRGKPF or a nucleotidic sequence encoding at least one of said amino-acids sequences, preferably the nucleotide sequence SEQ ID NO. 6: GAATTCCCACCATGGATCAG-
  TATATAAAAGCAAATTCTAAATTT ATAGG-
  TATAACTGAACTAGGAGGTTGCCATGGT-
  TCAGAACCATGTATCATTCATCGTGG
  TAAACCATTCGGCGGTTGTCACGGAAGT-
  GAGCCTTGCATTATACACAGAGGAAAGCCGT
  TCTAAGCGGCCGC.

Another aspect of the present invention is related to a pharmaceutical, cosmetical, food and/or feed composition comprising the compound according to the invention and a pharmaceutical, cosmetical, food and/or feed acceptable carrier.

Preferably, said pharmaceutical composition is a vaccine which may comprise a pharmaceutical acceptable carrier which can be any compatible non-toxic substance suitable for administering the composition (vaccine) according to the invention to a patient and obtain the desired therapeutical or prophylactic properties. The pharmaceutically acceptable carrier according to the invention suitable for oral administration are the ones well known by the person skilled in the art, such as tablets, coated or non-coated pills, capsules, solutions or syrups. Other adequate pharmaceutical carriers or vehicles may vary according to the mode of administration (cutaneous, epicutaneous, subcutaneous, intradermal, inhalation, patching, intravenous, intramuscular, parenteral, oral, etc.).

When the compound according to the invention is a nucleotidic sequence, the compound according to the invention can be administered naked or on a suitable pharmaceutical carrier such as a "vector" used for the transfection, transduction and expression of said sequence by a cell of the patient (including the expression and secretion outside the cell of the peptidic sequence encoded by said nucleotic sequence). Said "vector" is preferably selected from the group consisting of plasmids, viruses (retroviruses, adenoviruses, . . . ), lipidic vectors (such as cationic vesicles, liposomes, . . . ), molecules or devices which result in a chemical or a physical modification of the transfected cell (dextran phosphate, calcium phosphate, micro-injection device, electroporation device, etc.) or modified recombinant organisms comprising the compound according to the invention derived for instance from Salmonella or Mycobacteria strains, a nucleic acid encapsulated in the form of micro- or nanoparticles such as chirosan as described by Roy et al., *Nature Medicine* 5, pp. 387–391 (1999), etc.

The genetic modification of the patient's cell(s) for an ex vivo or in vivo treatment can be obtained by the person skilled in the art according to the known methods in the field of genetic therapy (such as the one described in the documents WO91/02805, WO91/18088, WO91/15501).

The pharmaceutical composition or the vaccine according to the invention may also comprise adjuvants (including helper viruses) well known by the person skilled in the art which may modulate the humoral, local, mucosal and/or cellular response of the immune system of a patient and improve the use of the compound according to the invention.

Adjuvants can be of different forms, provided they are suitable for administration to human beings. Examples of such adjuvants are oil emulsions of mineral or vegetal origin; mineral compounds such as aluminium phosphate or hydroxide, or calcium phosphate; bacterial products and derivatives, such as P40 (derived from the cell wall of Corynebacterium granulosum), monophosphoryl lipid A (MPL, derivative of LPS) and muramyl peptide derivatives and conjugates thereof (derivatives from mycobacterium components), alum, incomplete Freund's adjuvant, liposyn, saponin, squalene, etc. Recent reviews on adjuvants for human administration are described by Gupta R. K. et al. (*Vaccine* 11, pp. 293–306 (1993)) and by Johnson A. G. (*Clin. Microbiol. Rev.* 7, pp. 277–289 (1994)).

The pharmaceutical composition according to the invention is prepared by the methods generally applied by the person skilled in the art, for the preparation of various pharmaceutical compositions, especially vaccines, wherein the percentage of the active compound/pharmaceutically acceptable carrier can vary within very large ranges (generally a suitable dosage unit form contains about 0.005 µg to about 1 mg of compound per kg/body weight of patient), only limited by the tolerance and the level of accointance of the patient to the compound. The limits are particularly determined by the frequency of administration and by the specific diseases or symptoms to be treated.

Preferably, the compound is present in the pharmaceutical composition in a concentration which allows at least the reduction or suppression of the signs and symptoms of allergy or of a disease of allergic origin (preferably signs and symptoms of immediate hypersensitivity allergy).

The cosmetical composition according to the invention may comprise any cosmetical acceptable carrier selected according to the specific mode of administration. For instance, for skin hygiene, the cosmetical composition could be a product in the form of a cream, an ointment or a balsam.

The food or feed composition according to the invention could be any food, feed or beverage acceptable carrier comprising the usual liquid food or feed ingredients wherein the compound according to the invention is included.

Another aspect of the present invention is related to the use of the compound according to the invention as a medicament.

The present invention is also related to the use of the compound according to the invention or the pharmaceutical composition according to the invention for the manufacture of a medicament in the prevention and/or the treatment of allergy or of a disease of allergic origin, particularly immediate hypersensitivity allergy.

Another aspect of the present invention is related to a prevention and/or treatment method of allergy or of a disease of allergic origin, particularly immediate hypersensitivity allergy, comprising the step of administering the compound or the pharmaceutical composition according to the invention to a patient preferably a human patient, especially an atopic individual to an allergen, in order to elicit or increase advantageously the production of antibodies towards antigenic determinants of the allergen that are not spontaneously or only minimally recognised by the immune system of atopic individuals.

These diseases include rhinitis and sinusitis of allergic origin, bronchial asthma, atopic dermatitis, some forms of acute and chronic urticaria, gastro-intestinal syndromes associated with the ingestion of food allergens such as β-lactoglobulin, the so-called oro-pharyngeal syndrome of the same origin, anaphylactic reactions associated with drug hypersensitivity.

The present invention will be described in the following examples, in reference to the enclosed figures. These examples are presented as non-limiting illustrations of the various embodiments of the present invention.

BRIEF DESCRIPTION OF THE DRAWINGS

FIG. 5: Twenty-five ml of blood are collected by venous puncture in a henarinised tube and diluted twice with RPMI medium and laid on a Ficoll-Hypaque density gradient. The tubes are centrifuged for 20 min at 1,000 g. Cells from the interface are collected by aspiration and resuspended in RPMI, washed twice with the same medium and finally resuspended in the same medium at $10^6$ cells/ml. Fifty $\mu$l containing 10 $\mu$g/ml of either peptide 11–22 or 22–33 diluted in medium are added for an incubation of 6 days at 37° C. A positive control with PHA (10 $\mu$g/ml) is added. Proliferation of T cells is determined by assessing the extend of bromo-uridine (BrdU) incorporation in cell DNA, using an antibody specific for BrdU. results are shown in absorbency at 490 nm. No T cell proliferation above background value can be seen with peptide 11–22.

DETAILED DESCRIPTION OF THE INVENTION

Figure 1:
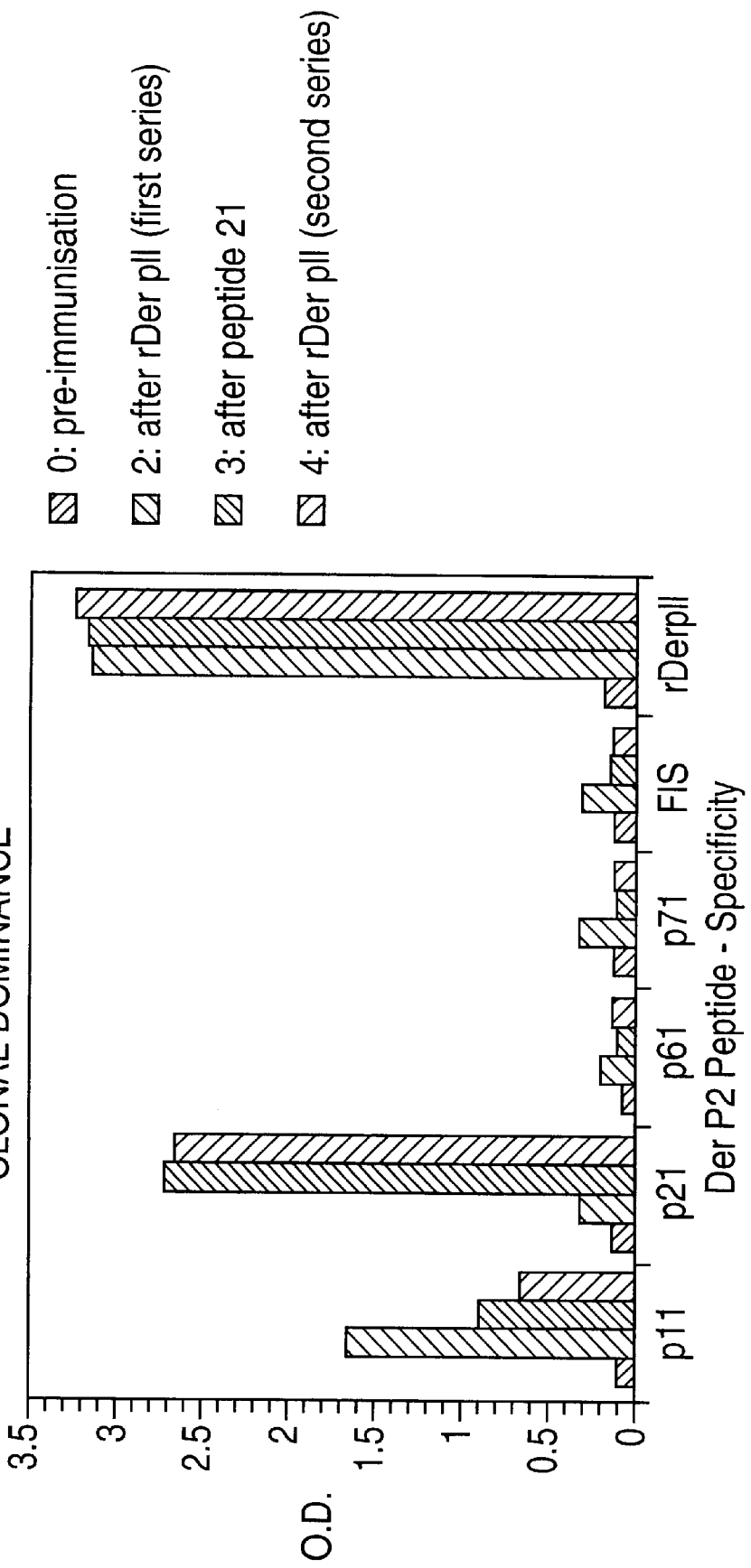
FIG. 1 represents Balb/c mice immunised by two SC injections of rDer pII (10 µg in Freund's adjuvant) administered at an interval of 2 weeks. The mice were bled and the reactivity of antibodies was evaluated using a set of overlapping peptides covering the Der pII sequence or the T cell adjuvant (FIS). Mice recognising peptide 11 (see point 2 in the Figure) were further immunised twice with 10 µg of peptide 21 and shown to recognise now peptide 21 with a 50% reduction in the concentration of antibodies to peptide 11 (point 3 in the Figure). Further administration of rDer pII maintains the reactivity to peptide 21, while further reducing the concentration of antibodies to peptide 11 (point 4).

Atopics as well as non-atopic subjects produce antibodies towards environmental allergens. These antibodies belong to all isotypes described so far, including IgE (Saint-Remy J. M. R. et al., *J. Immunol.* 43, pp. 338–347 (1988)). It is usually observed that atopic individuals produce 10 to 100-fold more IgE antibodies than non-atopic individuals, which can at least partly explain why atopics suffer from symptoms when encountering allergens to which they are sensitised.

It has been unexpectedly discovered that the antigenic determinants of allergens such as Der pI and Der pII—two of the main allergens of the house dust mite *Dermatophagoides pteronyssinus*—which are recognised by antibodies of atopics are not identical to those recognised by non-atopic individuals. This conclusion was reached by using a series of monoclonal antibodies raised in mice against purified Der pI or Der pII molecules. In a competition immunoassay, the Inventors have determined that some of the antigen determinants are recognised by anti-allergen antibodies from atopic individuals, while other determinants are recognised by anti-allergen antibodies produced by non-atopics. Further, they have shown that atopic patients whose allergic symptoms improved, either spontaneously or as a result of treatment, started producing antibodies to the very determinants recognised by non-atopic individuals, while reducing the production of initial antibodies.

The invention relates to the use of peptides derived from regions of allergen molecules that are recognised by antibodies made by non-atopics, or possibly regions which do not elicit a spontaneous antibody response. Administration of said peptides to atopic individuals results in the production of specific antibodies. Such antibodies will bind to the allergens whenever the patients are naturally exposed to them and, as a consequence, will restrict the access of antibodies made spontaneously by patients. Some atopic patients additionally produce a small proportion of antibodies to antigenic determinants recognised by non-atopics. In such cases, administration of the said peptides will increase the proportion of such antibodies so as to render them predominant in the anti-allergen immune response.

It is therefore the purpose of the present invention to provide a method by which the anti-allergen immune response is re-directed towards epitopes that are not spontaneously, or only minimally, recognised by antibodies produced by atopic patients.

The method of immunisation that is the object of the present invention provides several advantages over other methods.

Firstly, the immunisation procedure according to the invention is safe, as the peptides used do not carry determinants that can be recognised by IgE antibodies and have therefore no capacity to induce an anaphylactic reaction. This property contrasts with methods of immunisation using whole allergen molecules in their native or altered forms.

Secondly, the amount of immunising material and the number of injections required according to the invention are very much reduced as compared to alternative immunotherapeutic strategies, for the following reasons (1) as the peptides produced by the present invention do not contain IgE binding determinants, an immunogenic dose of peptide can be given at once, which therefore significantly shorten the length of treatment. Admixture or concomitant administration of an adjuvant can increase the immunogenicity of the peptides, further reducing the number of injections (and the amount of material required) to possibly a single one;

(2) as atopic individuals can in fact produce a small amount of antibodies directed to the epitopes recognised by non-atopic individuals, injection of peptides obtained by the present invention therefore boosts a secondary immune response (a secondary immune response will result in the production of much higher antibody titres than a primary immune response);

(3) as the administration of peptides alters the immune response to allergens at an early stage, namely the allergen recognition, processing by antigen-presenting cells and presentation to T cells, a limited amount of material will be all that is required to achieve the aim of the present invention.

The above-described characteristics represent a definite advantage over conventional desensitisation which has to be administered for several months or years and which makes use of high amount of allergens. In alternative therapies, such as the use of peptides to anergise T cells, the therapy requires much higher amounts of free peptides to compensate the high rate of peptide catabolism, and repeated administration is needed to maintain the anergic state.

Thirdly, continuing exposure to the allergens present in the natural environment of patients treated by the present invention is sufficient to maintain the immune response towards the antigenic determinants corresponding to peptides used for immunisation. Experimental evidence is indeed available showing that mice immunised with a peptide derived from a antigen maintain their reactivity towards the peptide upon subsequent challenge with the whole antigen (clonal dominance phenomenon) (Benjamini E. et al. *J. Immunol.* 141, pp. 55–63 (1988) and Schutze M. P. et al. *J. Immunol.* 142, pp. 2635–2640 (1989)) and enclosed FIG. 1).

The method according to the invention also represents a clear advantage over other therapies by which tolerance to allergens rather than immunisation towards novel antigenic determinants are sought. In the former, repeated administration of tolerogens is required to maintain the state of unresponsiveness.

The precise mode of action of the present invention is not yet completely elucidated.

The number of possible antigenic determinants is high that can be recognised by antibodies on allergens. However, allergens are usually small molecules, which restricts the number of antibody molecules which can bind to allergens at the same time. Antibodies which are present at the highest concentration and/or exhibiting the highest affinity will preferentially bind to the allergen. The same holds true for specific B cells, which express at their surface membrane an immunoglobulin molecule identical to the one they secrete. An antigen will therefore be captured by B cells which have the highest affinity and/or the highest frequency. This will prevent activation of B cells recognising other epitopes on the same molecule, a phenomenon which is called the "clonal dominance phenomenon" (Schutze M. P. et al. *J. Immunol.* 142, pp. 2635–2640 (1989)).

If one induces a preferential immune response in atopic individuals towards epitopes that are not or only weakly recognised by spontaneously formed antibodies, the clonal dominance phenomenon indicates that the anti-allergen immune response will now be directed to these new determinants and will decrease to antigenic determinants recognised initially. Two lines of experimental evidence support this concept. First, removal of an immunodominant B cell epitope on an antigen uncovers epitopes that were not recognised on the intact antigen and towards which the antibody response is now directed (Scheerlinck J. P. Y. et al., *Mol. Immunol.* 30, pp. 733–739 (1993)). Second, mice immunised with an antigen use only a fraction of their potential B cell repertoire to mount a specific immune response; immunisation with a peptide activates a selected repertoire of B cells, whose reactivity will be maintained even though the animal is challenged later with the native antigen (Benjamini E. et al. *J. Immunol.* 141, pp. 55–63 (1988)).

These two sets of experiments illustrate what is happening as a consequence of the compound administration according to the present invention. In further support of the concept of clonal dominance and its application to the allergy, Balb/c mice were injected with a recombinant (r) allergen, Der pII. The precise specificity of antibodies produced by such mice were determined by reaction with a panel of 15-mer peptides covering the entire Der pII sequence with a 5 aminoacid overlap.

In the example shown in FIG. 1, mice are producing antibodies to rDer pII and to peptide 11–25. Further immunisation with peptide 21–35 induces an immune response to 21–35 and a significant decrease of the binding to peptide 11–25. The immune response to Der pII is therefore redirected towards determinants that were not recognised first. Further, this experiment shows that the induced "re-directed" immune response resists further immunisation with the whole rDer pII allergen.

To be fully efficient, however, the peptide carrying a B cell epitope has to be administered together with an epitope that can be recognised by T cells, which will provide the B cells with the necessary signals to allow full differentiation into mature, antibody-producing plasmocytes. The T cell epitope does not have to be derived from the same molecule as the B cell. Therefore an hetero-peptide containing a B cell epitope derived from a given allergen and a T cell epitope of another origin will maintain the required specificity at the B cell level, while ensuring that the necessary signals provided by T cells are present. Such signals include the cognate B-T cell recognition and antigen non-specific signals such as interleukine production, CD40 interaction with its ligand, B7 (CD80) interaction with CD28 (Austyn & Wood, *Principles of Cellular and Molecular Immunology*, Oxford University Press (1993).

The T cell epitope (or epitopes) used for the present invention is selected according to its capacity to activate T cells of a majority of patients. Preferably, it is derived from an antigen commonly used for routine immunisation, such as tetanus toxoid or diphtheria antigen. This carries two main advantages. First, a number of universal, public T cell epitopes, namely, recognised by a vast majority of patients, have been described in such molecules (Reece J. C. et al., *J. Immunol.* 151, pp. 6175–6184 (1993)). Second, as virtually all individuals are vaccinated against tetanus toxoid or diphtheria, priming with the T cell epitope used for the present invention is already achieved, which should increase the efficacy of the vaccination, with possible reduction in doses and number of injections.

Peptides used for immunisation in the context of the present invention are preferably produced by synthesis (see for example Grant Editions, Synthetic Peptides) by an applied biosystem peptide synthesizer model 430 A or 431 or recombinant DNA techniques for their encoding nucleic acid sequences.

The composition containing the peptides is in a form suitable for injection by the subcutaneous, intramuscular or intradermal route. However, forms for inhalation, ingestion or direct application on skin or mucosa are possible.

The peptides can be in a linear or cyclic form, with or without additional moieties used, for instance, to block peptide-peptide interactions. Peptides can also be integrated into short peptide structures which force a specific 3-D conformation such as alpha-helix.

The composition can contain other material than the peptides, such as adjuvants.

The method as described in the present invention can be used to treat human or animal diseases in which IgE antibodies are demonstrated and deemed to play a role in the triggering of symptoms.

The present invention can be also applied to patients sensitive to allergens of animal or vegetal origin, or to chemical and pharmaceutical compounds like antibiotics (penicillin).

EXAMPLES

Example 1

A 31 amino-acid peptide made of 15 AA representative of a T cell epitope of tetanus toxoid (amino acids 830 to 844 of the heavy chain) and 14 AA containing a B cell epitope of Der pII, the two epitopes being separated by a stretch of two glycine residues, is obtained by synthesis. The sequence is SEQ ID NO 1 QYIKANSKFIGITELGGHEIKKV-LVPGCHGS.

Characteristics of the Peptide

1. The B Cell Epitope is not Recognised by IgE Antibodies

The peptide is not recognised by IgE antibodies made by individuals sensitive to the native protein. This is established by an immunoassay carried out as follows. The peptide is insolubilised on polystyrene microtitration plates and a panel of serum samples of atopic individuals sensitive to Der pII is added; the binding of specific IgE antibodies is detected by addition of an isotype-specific reagent.

Thus, a peptide (SEQ ID NO. 2) of the sequence HEIKKVLVPGCHGS corresponding to amino acids 11–24 of Der pII is obtained with solid-phase synthesis using methods well known to those skilled in the art with a biotin moiety added at its amino-terminal end. The peptide is insolubilised on neutravidin-coated plates and allowed to react with the serum of atopic individual. Results of such an experiment are shown in FIG. 2. Thus, the serum of an atopic individual with IgE antibodies towards Der pII was added to a neutravidin-coated plate which had been pre-incubated with 12-mer peptides covering the sequences 7–39 of Der pII with an 11 amino acid overlap. No binding above the background value was observed for any of the 22 peptides, indicating the absence of IgE antibodies capable to bind to such sequences.

2. The B Cell Epitope is Recognised by IgG Antibodies of Non-atopic Individuals

Figure 3:
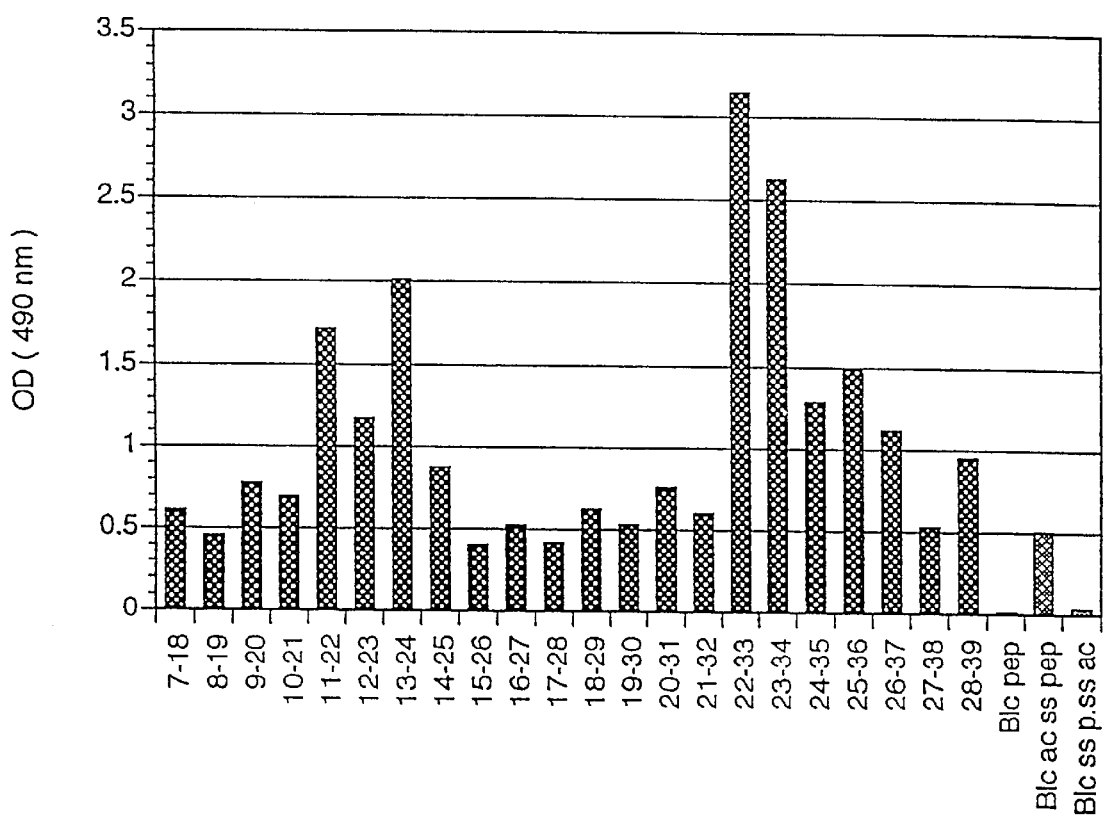
FIG. 3 represents an assay carried out as described in the legend to FIG. 2, except for the use of a 1/100 dilution of serum obtained from non atopic subjects and the use of goat antibodies to human IgG.

This was established using a similar assay procedure as described above for IgE antibodies, except that a goat anti-human IgG antibodies was used for the detection of IgG antibodies and that a 1/100 dilution of serum was used. Representative results of such an experiment are given in FIG. 3, from which it can be seen that significant binding occurred in between amino acid 11 and 24, as well as in between amino acid 22 and 34. The 7–39 region of Der pII therefore contains two binding sites for IgG of non-atopic individuals.

3. The B Cell Epitope is not Recognised by IgG Antibodies of Atopic Individuals

Figure 4:
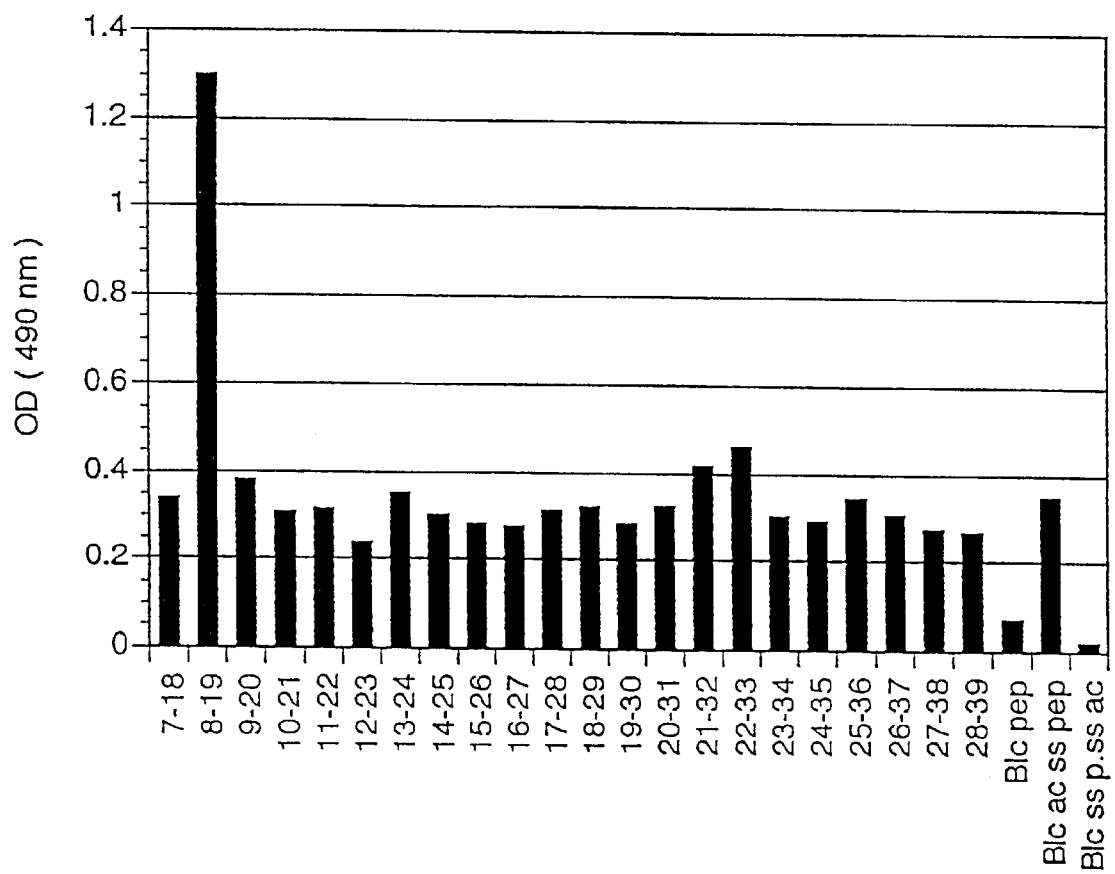
FIG. 4 represents an assay carried out exactly as described for FIG. 3, except for the use of serum obtained from atopic subjects.

This was established using an assay procedure identical to the above-described assay for non-atopic subjects, except that the serum is now obtained from Der pII-hypersensitive patients. The results as shown in FIG. 4 indicate that IgG of atopic individuals do not bind to the 11–24 Der pII region. A minority of patients have antibodies reacting with the 8–19 peptide.

4. The 11–24 Der pII Region does not Contain a T Cell Epitope

This was established by T cell proliferation assays using methods well known for those skilled in the art (see for instance *Current Protocols in Immunology*, eds Coligan J E, Kruisbeek A M, Margulies D H, Shevach E M and Strober W, Chapter 3, Greene Publishing Associates & John Wiley & Sons, 1992–1998). Peripheral blood mononucleated cells (PBMC) are separated from whole blood by density gradient centrifugation. The PBMC suspension is then incubated for 4 to 6 days with either rDer pII or with a 12-mer peptide included in the 7–39 region of Der pII. Results shown in FIG. 5 indicate that addition of peptide 11–22 to the PBMC suspension did not result in proliferation of T cells, whereas significant proliferation was observed with peptide 22–33 and with PHA, the latter being used as a positive control.

Use of the Hybrid Peptide

The peptide (SEQ ID NO. 1) is mixed with an adjuvant suitable for human administration in order to increase its immunogenicity. Thus, muramyl-dipeptide (MDP) is used and covalently coupled to the peptide according to published methods (Matsumoto K. et al., *Immunostimulants: Now and Tomorrow*, Eds I. Azuma and G. Jolles, pp. 79–97 (1987), Japan Sci. Soc. Press, Tokyo/Springer-Verlag, Berlin).

The mixture containing the peptide and MDP is then administered to a patient sensitive to Der pII. Thus, a suspension containing 100 μg/ml of peptide in made in saline containing 0.3% human serum albumin and 0.4% phenol. One ml of the solution is injected in the arm by the subcutaneous route.

Example 2

The compound of the invention can be prepared by recombinant cDNA technology to produce a polypeptide made of a series of repetitive units of T and B cell epitope-containing peptides. A polypeptide made of a duplicated T cell epitope derived from TT (amino acids 830 to 844 of the heavy chain) and six repetitive B cell epitopes derived from Der pI I is produced by DNA technology. A sequence of two amino acid residues is inserted in between each epitope. The sequence is: D-(QYIKANSKFIGITELX)$_2$-(CHGSEPCIIHRGKPFX)$_5$-CHGSEPCIIHRGKPFSR, (SEQ ID NO. 3), in which X is GG or SS.

Such polypeptide is obtained as follows. The nucleotide sequence of the TT epitope corresponding to QYIKANSKFIGITEL (SEQ ID NO. 13) and of the Der pII epitope 21–35 corresponding to CHGSEPCIIHRGKPF (SEQ ID. NO. 14) are deduced. A theoretical assembly is made from nucleotides corresponding to, on the one hand, the sequence TT epitope—GG—TT epitope (T subunit) and, on the other hand, two copies of the Der pII epitope separated by a GG sequence (B subunit). Oligonucleotides covering the entire sequence of each subunit (one T subunit and one B subunit) are synthesised. The complete DNA sequence coding for the two subunits is obtained by PCR.

For the two TT subunits, the sense primer is: GTATCTCTCGAGAAAAGAGATCAATA-CATTAAGGCTAACAGTAAGTTCATTGG (SEQ ID NO. 7); and the antisense primer is AAACAGCCTCTA-GAGAGTTCGGTAATGC-CGATAAACTTTGAATTGGCTTTGATGTACTG ACCGCCAAGCTCTGTGATTCCAAT-GAACTTACTGTTAGCC (SEQ ID NO. 8).

For the two B subunits, the sense primer is: GTATCTAC-TAGTTGCCATGGTTCAGAACCATGTAT-CATTCATCGTGGTAAACCATTCGG CGGTTGTCACG-GAAGTGAGCCTTGCATTATACACAGAGGAAAGC (SEQ ID NO. 9); and the antisense primer is: CGTATGT-GTCGACCCGCTATCTAGAGAACG-GCTTTCCTCTGTGTATAATGC (SEQ ID NO. 10).

The full DNA sequence corresponding to the polypeptide is obtained by directional multimerization of subunits, using sequences flanked by restriction enzyme sites which generate compatible ends.

The sequence of the final 137 amino acid polypeptide is: DQYIKANSKFIGITELGGQYIKAN-SKFIGITELSSCHGSEPCIIHRGKPFGGCHGSEPC IIHRGKPFSSCHGSEPCIIHRGKPFG-GCHGSEPCIIHRGKPFSSCHGSEPCIIHRGKPF GGCHGSEPCIIHRGKPFSR (SEQ ID NO. 3).

Figure 2:
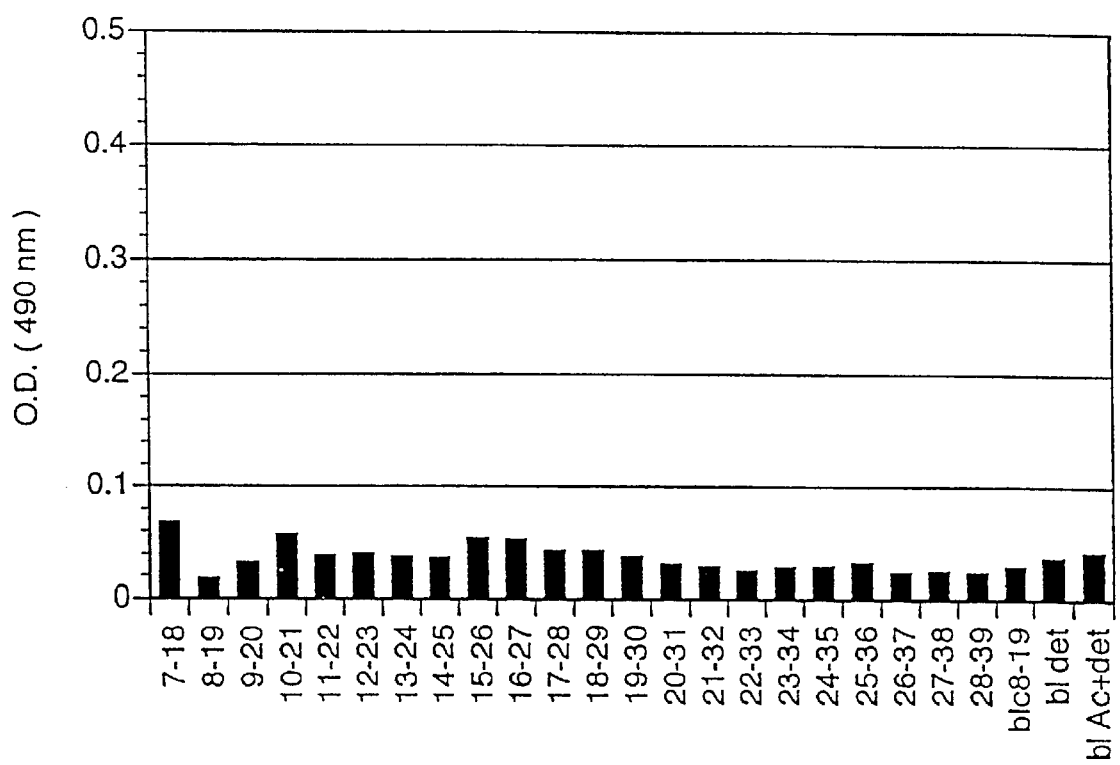
FIG. 2 represents biotin-labelled peptide diluted in phosphate buffered saline, pH 7.4 (PBS) to a concentration of 2 µg/ml. Fifty µl of this dilution are added to neutravidin-coated plates and incubated for 1 h at room temperature (RT). The plates are washed with PBS and residual binding sites saturated by addition of 100 µl of casein diluted to 5 mg/ml in PBS. After 30 min at RT, the plate is washed again and incubated for 2 h at RT with a ⅕ dilution of serum from an atopic individual, washed again and incubated with goat antibodies specific for human IgE which are coupled to peroxidase. After a new washing the plate is incubated with a substrate for the enzyme which is coloured after enzymatic cleavage. The intensity of the coloration in the wells (shown by absorbency at 490 nm on the Y axis) is proportional to the amount of specific IgE antibodies present in the serum sample. Control assays included the no peptide or no antibody dilution.

The peptide CHGSEPCIIHRGKPF (SEQ ID NO. 14), which corresponds to the 21–35 amino acid sequence of Der pII does not contain an IgE-binding epitope, as demonstrated in a similar assay as that described in FIG. 2. It does however contain an epitope recognized by IgG antibodies of non-atopic individuals, but not of atopic subjects, as shown using assay systems similar to the ones described in FIG. 3 and FIG. 4, respectively.

The 137 amino acid polypeptide is produced in cultures of yeast using a methodology well known by those skilled in the art, and which can be found in reference texts such as Current Protocols in Molecular Biology, eds Ausubel F M, Brent R, Kingston R E, Moore D D, Seidman J G, Smith J A and Struhl K, Chapter 16.13, John Wiley & Sons, 1994–1997. The polypeptide is adsorbed on aluminium hydroxide and is administered by subcutaneous injection at a dose of 100 μg. Two injections are given at an interval of 3 weeks.

Example 3

The nucleotide sequence coding for compound of the invention can be used for direct gene immunization. This DNA-based vaccine can be administrated by different routes (i.e. intramuscular, intradermal, subcutaneous, oral) using "naked" DNA, encapsulated DNA or DNA in the form of micro- or nanoparticles such as chitosan (K. Roy et al, Nature Medicine 1999; 5: 387–391).

A nucleotide construction made as in Example 2 but containing the DNA sequence coding for one T cell epitope derived from TT and 2 B cell epitopes derived from Der pII, each epitope being separated by the sequence GGAGGT or GGCGGT coding for 2 glycine residues, is used for direct immunization by intramuscular injection. The nucleotide sequence is flanked in 5' by a sequence containing an EcoRI restriction site and a KOZAK sequence (i.e. GAATTC-CCACCATGG (SEQ ID NO. 14)) and in 3' by a stop codon and a NotI restriction site (i.e. TAGGCGGCCGC (SEQ ID NO. 15)), and inserted into a suitable vector.

The sense primer is: CCGGAATTCCCACCATGGAT-CAGTATATAAAAGCAAATTCTAAATT-TATAGGTATAACT GAACTAGGAGGTTGCCATGGT-TCAGAACCATGTATCATTCATCG (SEQ ID NO. 11); and the antisense primer is: TCGAGCGGCCGCTTAGAACG-GCTTTCCTCTGTGTATAATGCAAGGCT-CACTTCCGTGAC AACCGCCGAATGGTTTACCAC-GATGAATGATACATGGTTCTGAACC (SEQ ID NO. 12).

The construction of sequence GAATTCCCACCATG-GATCAGTATATAAAAGCAAAT-TCTAAATTTATAGGTATAACTGAA CTAGGAGGT-TGCCATGGTTCAGAACCATGTATCATTCATCGTGGT AAACCATTCGGCGG TTGTCACGGAAGTGAGCCT-TGCATTATACACAGAGGAAAGCCGT-TCTAAGCGGCCGC (SEQ ID NO. 6) is used for mouse immunization. Six Balb/c mice are primed with TT at day −7. At day 0, mice are anesthesized and IM injections of 100 μg DNA are made at two weeks intervals. Mice are bled after three injections and the serum is evaluated for the presence of antibodies to the B cell epitope produced from the DNA construct and to the full-length native Der pII molecule.

Example 4

A 40 amino-acid peptide made of 13 AA representative of a T cell epitope of the influenza A virus, a GKKG sequence corresponding to a canonical protease sensitive site, a repeated identical T cell epitope, a second GKKG, and 6 AA containing a B cell epitope of Der pI is obtained by synthesis. The sequence is PKYVKQNTLKLATGKKGP-KYVKQNTLKLATGKKGVIIGIK (SEQ ID NO. 4).

The same characteristics as in example 1 are demonstrated using similar assay systems.

Example 5

The wild-type sequence of the B cell epitope-containing moiety can be altered in such a way as to eliminate an intrinsic T cell epitope while maintaining full immunogenicity of the B determinant, thanks to the presence of another functional T cell epitope within the immunizing peptide.

Thus, a 32 amino-acid long peptide of sequence QYI-KANSKFGITELGGCHGSEPCNIHRGKPF (sequence ID No. 5) is produced by synthesis as in Example 1. This peptide corresponds to a T cell epitope derived from TT (amino acid 830 to 844) and a B cell epitope derived from Der pII separated by a stretch of GG. The B cell epitope sequence has a point substitution in position 28, i.e. a substitution of I to N, which was shown to eliminate a major T cell epitope by assay systems as described in FIG. 5.

The peptide is used for mouse immunization. Thus, six BALB/c mice are injected in each footpad with 50 μl of an emulsion containing 50 μg of the peptide in complete Freund's adjuvant. The same injection procedure is used twice at a fortnight interval, except for the use of incomplete Freund's adjuvant. Two weeks after the last injection, the mice are bled and the serum shown to contain specific antibodies to the Der pII B cell epitope included in the synthetic peptide used for immunization, and to full-length Der pII protein. Regional draining lymph nodes are obtained for the preparation of T cell suspension. The latter are shown to proliferate in the presence of TT, but not in the presence of Der pII or the peptide corresponding to the B cell moiety used for immunization.

Example 6

Multiple antigenic peptides can be used for immunization with the advantage of increased immunogenicity and the possibility of using an immunogen containing B epitopes derived from different, possibly unrelated allergen molecules. Multiple antigenic peptides, or branched peptides, are synthesized according to methods known by those skilled in the art. Appropriate description of the methodology can be found for instance in Tam J. P., *Proc. Natl. Acad. Sci USA* 1988; 85: 5409–5413.

A core peptide made of 8 lysine (K) residues is made synthetically. Each K epsilon-amine group can be substituted by a particular peptide attached to the K backbone by a peptidic link. Thus, the first 2 residues are substituted with the sequence QYIKANSKFIGITEL (SEQ ID NO. 13) corresponding to the T cell epitope of TT (amino acid 830 to 844). Residues 3 and 4 are substituted with the sequence CHGSEPCNIHRGKPF (SEQ ID NO. 14) corresponding to the Der pII-derived B cell epitope with a I28N point substitution. Residues 5 and 6 are substituted with the sequence VIIGIK containing a B cell epitope derived from Der pI as shown in Example 4. Residues 7 and 8 are substituted with the sequence PKYVKQNTLKLAT (SEQ ID NO. 18) corresponding to a major T cell epitope of the influenza A virus.

The substituted branched peptide is used to immunize BALB/c mice by the same procedure as described in Example 5. The serum is shown to contain antibodies to full-length Der pII and Der pI proteins and to the two B cell epitopes derived from these two allergens. T cell proliferation assays show a positive response to TT and to the influenza A viral protein containing the T cell epitope sequence.

Example 7

The nucleotide sequence coding for compound of the invention can be administered by gene transfer technology using recombinant viral or non-viral vectors (e.g. artificial lipid bilayers), molecular conjugates or modified recombinant organisms derived for instance from salmonella or mycobacteria.

Thus, an adenoviral vehicle containing the same DNA sequence as in Example 3 is engineered. This vector is prepared from two components: adenoviral DNA vector (Ad5 E1-E3-) and a packaging cell line. The sequences coding for one T cell epitope and two B cell epitopes are first inserted into the pAd plasmid. The linearized chimeric plasmid is then co-transfected using conventional DNA transfer techniques with the restricted Ad genoma into E1 transcomplementing 293 packaging cells for in vivo homologous recombination.

Viral stock prepared in 293 cells give titers ranged from $3 \times 10^{10}$ to $2 \times 10^{11}$ plaque-forming units per ml (pfu/ml).

$10^7$ pfus are administered by inhalation in BALB/c mice. Mice are bled three weeks after and the level of antibodies towards Der pII, and the B cell moiety contained in the immunizing construct is evaluated by direct binding ELISA as in FIG. 3.

Example 8

The immunogenicity for humans of the compound of the invention can be evaluated in a humanized animal model. Thus, severe combined immunodeficiency (SCID) mice are reconstituted with immunocompetent cells of human origin.

Peripheral blood mononuclear cells (PBMC; 15×10⁶ per mouse) obtained from an atopic donor sensitive to Der pII are injected into the peritoneum of each SCID mouse. Six mice reconstituted in such a way are injected at day 1, 15 and 30 with 50 μg of the recombinant polypeptide described in example 2. Mice are bled before and six weeks after the start of the immunization procedure. The serum is evaluated for the presence of antibodies to the recombinant polypeptide and found negative before and positive after immunization using a direct binding assay similar to that described in FIG. 4.

Example 9

Cosmetic Composition for Skin Hygiene

|  | % weight |
| --- | --- |
| Oil phase |  |
| BRIJ 721 (Steareth 21) | 4.00 |
| Cetyl alcohol | 10.00 |
| Mineral oil | 5.00 |
| Propyl parahydroxybenzoate | 0.02 |
| Water phase |  |
| CARBOPOL 943 (Carbomer 934) | 0.10 |
| Sodium hydroxide (solution at 10%) | 0.10 |
| Methyl parahydroxybenzoate | 0.18 |
| Compounds according to the example 1 to 3 | 0.50–5.00 |
| Demineralised water | 75.60–80.10 |
| Total: | 100 |

The cosmetical composition according to the invention can be used in a cream form directly upon the skin of the patient. The compounds according to the invention can be also incorporated into the oil phase instead of being dissolved in the water phase.

Example 10

Food Composition (Acidified Whey Milk)

A whey milk comprising Lactobacillus strain and two Streptococcus strains traditionally used for the production of yoghurt, was obtained from a lactoserum powder reconstituted at 12.5% in water. 40 l of this whey were pasteurised at about 92° C. for 6 min, homogenised at about 75° C. and 150 bars (two levels) and cooled at temperature about 42° C.

The whey milk having incorporated the compound according to the invention (peptides of the example 1 to 3) was incubated at 42° C. and at a pH of around 5 and then cooled at temperature about 5° C.

Said food composition according to the invention is used directly by the patient by oral administration.

What is claimed is:

1. An isolated compound consisting of one of the following amino acid sequences selected from the group consisting of SEQ ID NO. 1, SEQ ID NO. 3, SEQ ID NO. 4 and SEQ ID NO. 5.

2. A method for treating an allergy against a house dust mite *Dermatophagoides pteronyssinus*, which comprises administering the compound according to claim 1, to a patient in need thereof.

3. A pharmaceutical composition comprising the compound according to claim 1 and a pharmaceutically acceptable carrier.

4. A cosmetical composition comprising the compound according to claim 1 and a cosmetical acceptable carrier.

5. A beverage, food or feed composition comprising the compound according to claim 1 and a liquid, food or feed acceptable carrier.

6. The compound according to claim 1, which is used as a medicament.

7. The compound according to claim 1, which is used to treat an allergy against a house dust mite *Dermatophagoides steronyssinus*.

* * * * *